United States Patent [19]

Burley

[11] 4,167,520
[45] Sep. 11, 1979

[54] PROCESS FOR PREPARING ORGANOTIN TRIHALIDES

[75] Inventor: Joseph W. Burley, Wallasey, England

[73] Assignee: Akzo N.V., Arnhem, Netherlands

[21] Appl. No.: 901,224

[22] Filed: Apr. 28, 1978

Related U.S. Application Data

[63] Continuation of Ser. No. 760,329, Jan. 18, 1977, abandoned.

[30] Foreign Application Priority Data

Jan. 23, 1976 [GB] United Kingdom ............... 2658/76

[51] Int. Cl.² .................................................. C07F 7/22
[52] U.S. Cl. ...................................................... 260/429.7
[58] Field of Search ........................................ 260/429.7

[56] References Cited

U.S. PATENT DOCUMENTS

| | | | |
|---|---|---|---|
| 3,161,664 | 12/1964 | Depree | 260/429.7 |
| 3,398,169 | 8/1968 | Neumann et al. | 260/429.7 |
| 3,403,169 | 9/1968 | Rudner et al. | 260/429.7 X |
| 3,412,122 | 11/1968 | Considine et al. | 260/429.7 |
| 3,440,255 | 4/1969 | Matsuda et al. | 260/429.7 |
| 4,080,362 | 3/1978 | Hutton et al. | 260/429.7 |

OTHER PUBLICATIONS

Omae et al, J. Organometallic Chem., 24, pp. 663–666, (1970).
Matsuda et al, J. Organometallic Chem., 25, pp. 101–109, (1970).
Sawyer, Organotin Compounds, Marcel Dekker Inc., N.Y., pp. 90 & 91, (1971).

Primary Examiner—Helen M. S. Sneed
Attorney, Agent, or Firm—Stevens, Davis, Miller & Mosher

[57] ABSTRACT

This invention provides a process for preparing organotin trihalides which comprises reacting tin tetrahalide with an organotin dihalide of general formula $R_2SnHal_2$ wherein Hal denotes a halogen atom and R represents the group

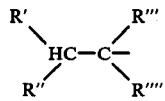

wherein R', R", R'" and R"" are each independently a hydrogen atom or an alkyl or substituted alkyl group having 1 to 18 carbon atoms with the proviso that at least one of R' and R" contains adjacent to the group HC— a carbonyl group which forms a part of an acid group, ester group, aldehyde group, acid halide group or ketone group, and recovering the organotin trihalide of formula $RSnHal_3$ thereby formed.

2 Claims, No Drawings

PROCESS FOR PREPARING ORGANOTIN TRIHALIDES

This is a continuation of application Ser. No. 760,329 filed Jan. 18, 1977, now abandoned.

The present invention relates to a process for the preparation of organotin compounds and in particular to the preparation of organotin halides.

Organotin halides are normally prepared from a tetraalkyl tin compound by disproportionation with tin tetrahalide according to the following equation:

$$R_4Sn + SnHal_4 \rightarrow 2R_2SnHal_2.$$

In this equation R represents an alkyl group, such as a butyl or octyl group, and Hal represents a halogen atom, preferably chloride. At a temperature of about 160° C. the reaction goes virtually to completion.

The organotin dihalides are well-known and important intermediates in the preparation of stabilizer compounds for vinyl polymers which contain halides such as polyvinyl chloride.

Organotin trihalides are also intermediates in the preparation of stabilizer compounds, but their preparation by a similar disproportionation reaction is much less straight forward.

The disproportionation reaction described above actually proceeds in two stages:

$$R_4Sn + SnHal_4 \rightarrow RSnHal_3 + R_3SnHal \qquad (I)$$

$$RSnHal_3 + R_3SnHal \rightarrow 2R_2SnHal_2 \qquad (II)$$

Since reaction (I) occurs at room temperature, it is theoretically possible to obtain organotin trihalides by carefully separating this reaction from reaction (II) which requires a higher temperature of about 160° C. However, in practice the simultaneous formation of the unwanted monohalide presents a purification problem and in fact a loss in tin values.

Starting from the same reactants, the formation of organotin trihalides should, in principle, be favored by altering the relative proportions of the reactants according to the equation:

$$R_4Sn + 3\ SnHal_4 \rightarrow 4RSnHal_3 \qquad (III)$$

This reaction, which takes place at a temperature of about 100° C., does not however proceed satisfactorily, because the reaction product always contains unconverted dihalides with attendent loss in tin values. It is clear that the further disproportionation reaction $$R_2SnHal_2 + SnHal_4 \rightarrow 2RSnHal_3 \qquad (IV)$$

does not proceed satisfactorily and accordingly prevents the desired trihalides from being obtained in satisfactory yield and quality. Indeed, when reaction (IV) is repeated separately starting from pure alkyl tin dihalides very low yields of only a few percent are obtained, even after ten hours reaction at 150° C.

It has now been found surprisingly that reaction (IV) proceeds satisfactorily to give high yields of trihalides when instead of representing an alkyl group the group R is selected from a certain group of functionally substituted alkyl residues.

It is therefore an object of this invention to provide an improved process for preparing organotin trihalides by reacting a tin tetrahalide with an organotin dihalide. Another object of the invention is to provide an organotin stabilizer for a polyvinyl halide polymer such as polyvinyl chloride and a polyvinyl halide polymer containing an organotin trihalide.

Accordingly, the present invention provides a process for the preparation of organotin trihalides which comprises reacting tin tetrahalide with an organotin dihalide of general formula $R_2SnHal_2$ wherein R represents the group

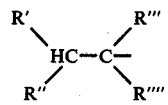

wherein R', R", R''' and R'''' are each independently a hydrogen atom or an alkyl or substituted alkyl group having from 1 to 18 carbon atoms with the proviso that at least one of R' and R" contains adjacent to the group HC— a carbonyl group which forms a part of an acid group, ester group, aldehyde group, acid halide group or ketone group.

The organotin dihalides $R_2SnHal_2$ wherein R represents the above identified group and their method of preparation are more fully described in U.S. patent application Ser. No. 660,631, filed Feb. 23, 1976, the disclosure of which is incorporated herein by reference.

The corresponding organotin trihalides $RSnHal_3$ which are formed by the method of this invention are specifically described in U.S. patent application Ser. No. 613,434, filed Sept. 12, 1975. The present disproportionation reaction is of industrial importance as an alternative route to the desired trihalides, as prepared by the method described in the latter patent application.

While the halogen atom, Hal, in the halide reactants may be either chloride, bromide or iodide, the chlorides are generally preferred.

Examples of substituted alkyl residues for the group R in the organotin dihalides are those derived from olefinic compounds such as acrylic acid, acrylate esters, acryloyl halides and vinyl alkyl ketones such as methyl acrylate, methyl crotonate, methyl 2-cyclohexyl acrylate, cinnamic acid, cinnamic methyl ester, acryloyl chloride, 1,1 bis(carboxyethyl) propylene, methyl vinyl ketone, mesithyl oxide, and methyl styryl ketone.

Accordingly, the process of this invention is preferably performed using an olefin of the above formula wherein at least one of $R_1$ and $R_2$ is an oxygen-containing group having the formula

where $R_5$ is hydrogen, hydroxyl, halogen, amino or alkyl, substituted alkyl or alkoxy containing 1–18 carbon atoms.

The preparation of organotin trihalides according to reaction (IV) and starting from organotin dihalides wherein R is a group as hereinbefore defined is illustrated in the following Examples.

EXAMPLE I 150 g of $(C_4H_9OCOCH_2CH_2)_2SnCl_2$ and 79.8 g of tin tetrachloride were charged to a 500 ml three neck flask equipped with stirrer, thermometer, condenser and heating mantle.

The reagents were stirred and the temperature maintained at 100° C. for 9 hours. After this time the reaction mixture was found by analysis to consist of an almost quantitative yield of $C_4H_9OCOCH_2SnCl_3$.

The above procedure was repeated maintaining higher temperatures for shorter reaction times, namely 120° C. for 3 hours, 140° C. for 2 hours and 150° C. for one hour, which also resulted in a virtually quantitative yield of the above organotin trihalide.

EXAMPLE II 100 g of $(CH_3OCOCH_2CH_2)_2SnCl_2$ and 71.5 g of tin tetrachloride were charged to a reaction vessel equipped as in Example I. The reaction mixture was stirred and the temperature maintained at 100° C. for 11 hours. After this time the reaction mixture was found to consist entirely of $CH_3OCOCH_2CH_2SnCl_3$.

EXAMPLE III 100 g of $(C_{18}H_{37}OCOCH_2CH_2)_2SnCl_2$ and 31.0 g of tin tetrachloride were charged to a reaction vessel equipped as in Example I. The reaction mixture was stirred and the temperature maintained at 140° C. for 8 hours. After this time analysis indicated that the reaction mixture contained about 77 wt. % of $C_{18}H_{37}OCOCH_2CH_2SnCl_3$.

EXAMPLE IV 90.5 g of $(CH_3OCOCH_2CH_2)_2SnBr_2$ and 52.1 g of tin tetrabromide were charged to a reaction vessel equipped as in Example I. The reagents were stirred and the temperature maintained at 140° C. for 10 hours. After this time the reaction mixture was shown by analysis to consist almost entirely of $CH_3OCOCH_2CH_2SnBr_3$.

The present invention also includes within its scope organotin trihalides $RSnHal_3$, wherein R is as defined above, when prepared by the process of the invention. The invention furthermore includes within its scope stabilizer compounds for halide containing vinyl polymers when prepared from these organotin trihalides.

Although the invention has been described in detail for the purpose of illustration, it is to be understood that such detail is solely for that purpose and that variations can be made therein by those skilled in the art without departing from the spirit and scope of the invention except as it may be limited by the claims.

I claim:

1. A process for the preparation of organotin trihalides which comprises reacting tin tetrahalide with an organotin dihalide of the general formula $R_2SnHal_2$ according to the reaction:

$$R_2SnHal_2 + SnHal_4 \rightarrow 2RSnHal_3$$

wherein Hal denotes a halogen atom and R represents a monovalent residue derived from an olefinic compound selected from the group consisting of acrylic acid, acrylate esters, acryloyl halides and vinyl alkyl ketones.

2. The process of claim 1 wherein the halide reactants are chlorides.

* * * * *